United States Patent [19]

Kaye et al.

[11] Patent Number: 4,531,938

[45] Date of Patent: Jul. 30, 1985

[54] MEDICAMENT IMPLANT APPLICATOR

[75] Inventors: Gordon E. Kaye, Garrison, N.Y.;
Eugene B. Schwartz, Miami Beach,
Fla.; Irving V. Sollins, Jiutepec
Morelos, Mexico

[73] Assignee: Ivy-Gene Co., Inc., Washington, D.C.

[21] Appl. No.: 511,251

[22] Filed: Jul. 6, 1983

[51] Int. Cl.³ .............................................. A61M 5/00
[52] U.S. Cl. ..................................... 604/62; 206/528;
221/81; 221/88
[58] Field of Search ............................ 604/60, 59–61,
604/63, 64, 241; 124/48, 95; 221/78, 79, 81, 88;
206/3, 528, 538, 343

[56] References Cited

U.S. PATENT DOCUMENTS 3,774,607 11/1973 Schmitz ............................ 604/62 X
4,077,406 3/1978 Sandhage et al. ................. 604/62 X
4,400,170 8/1983 McNaughton et al. .............. 604/62

Primary Examiner—Stephen C. Pellegrino
Attorney, Agent, or Firm—Fidelman, Wolffe & Waldron

[57] ABSTRACT

The present invention relates to an implanter device adapted for insertion of a solid or semi-solid pellet form medicament into a domestic animal, and to an encasement containing a multiplicity of dosage unit pellets of the medicament. The encasement is specifically adapted for use in the implanter device.

6 Claims, 13 Drawing Figures

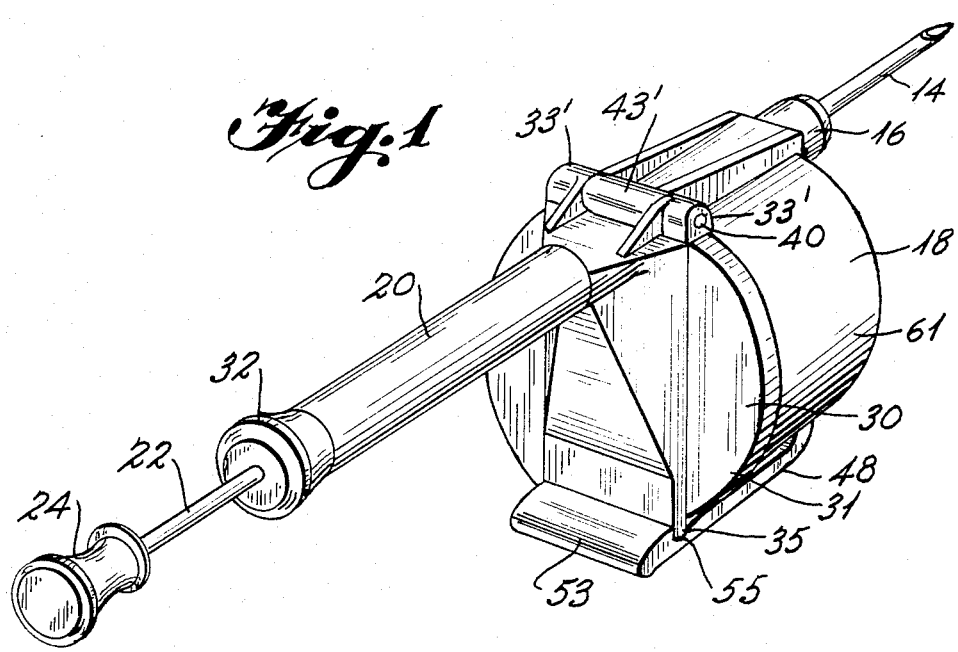
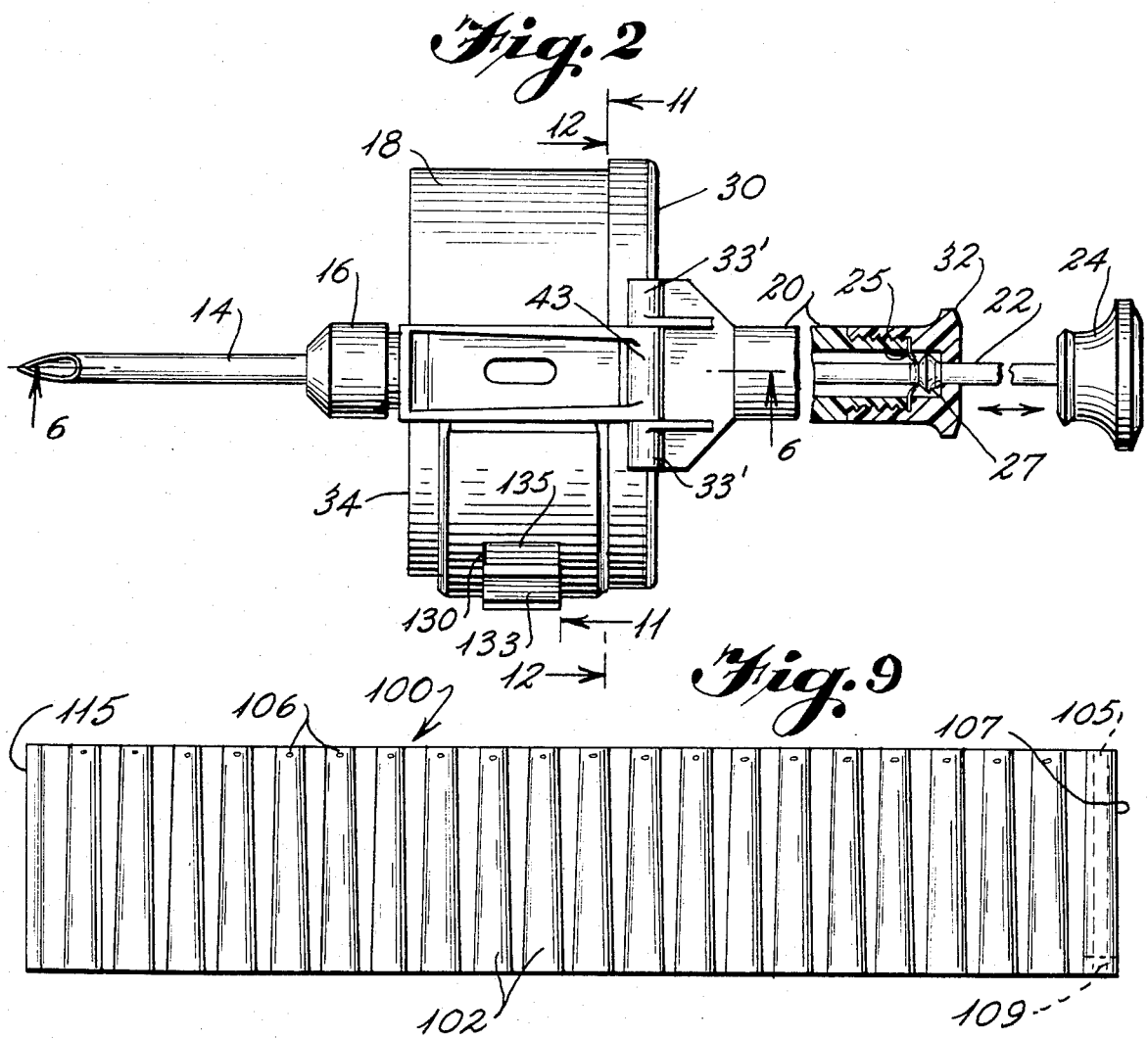

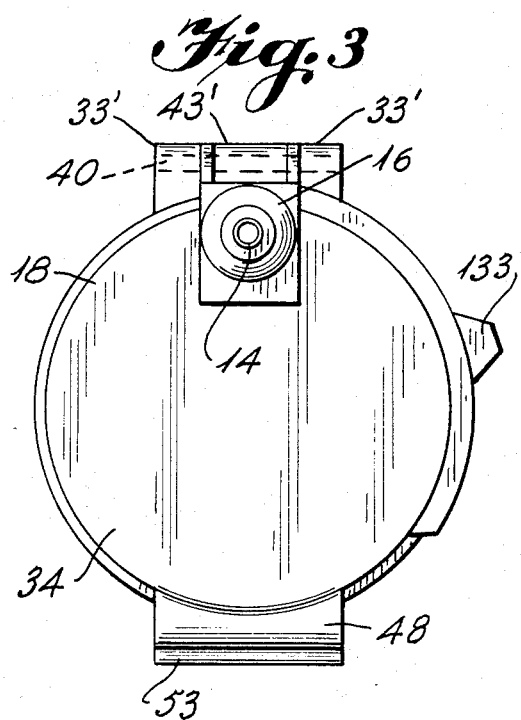
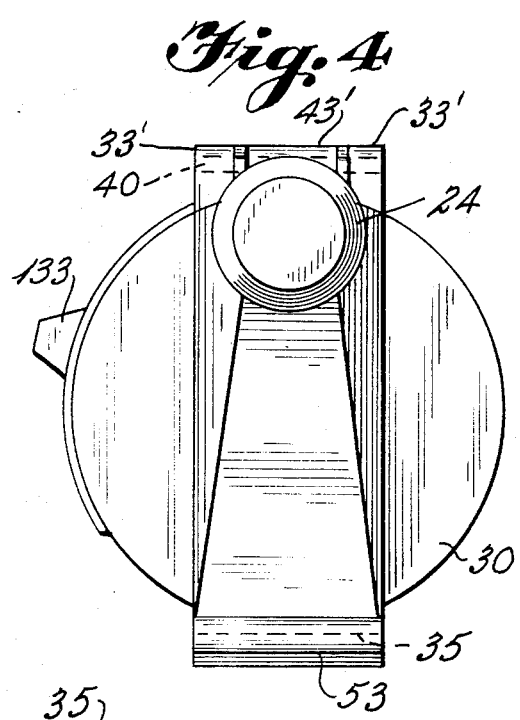
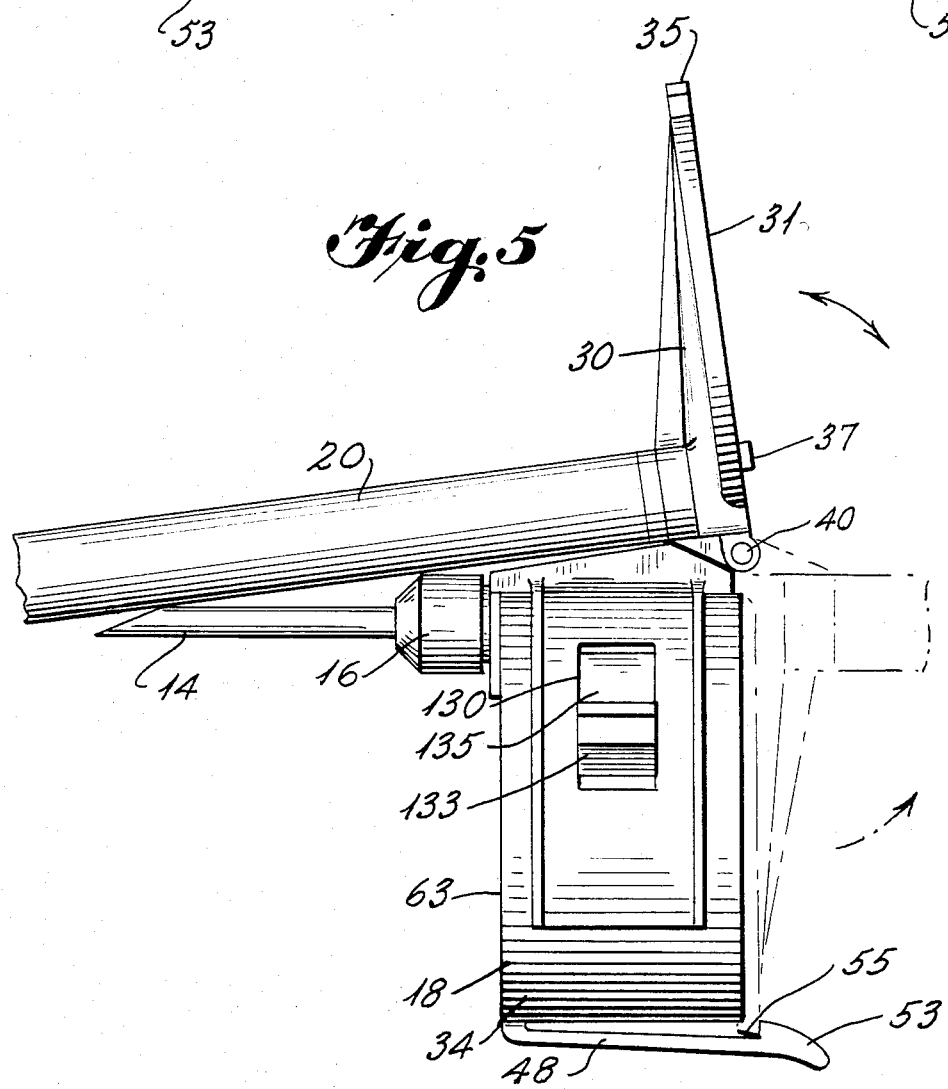

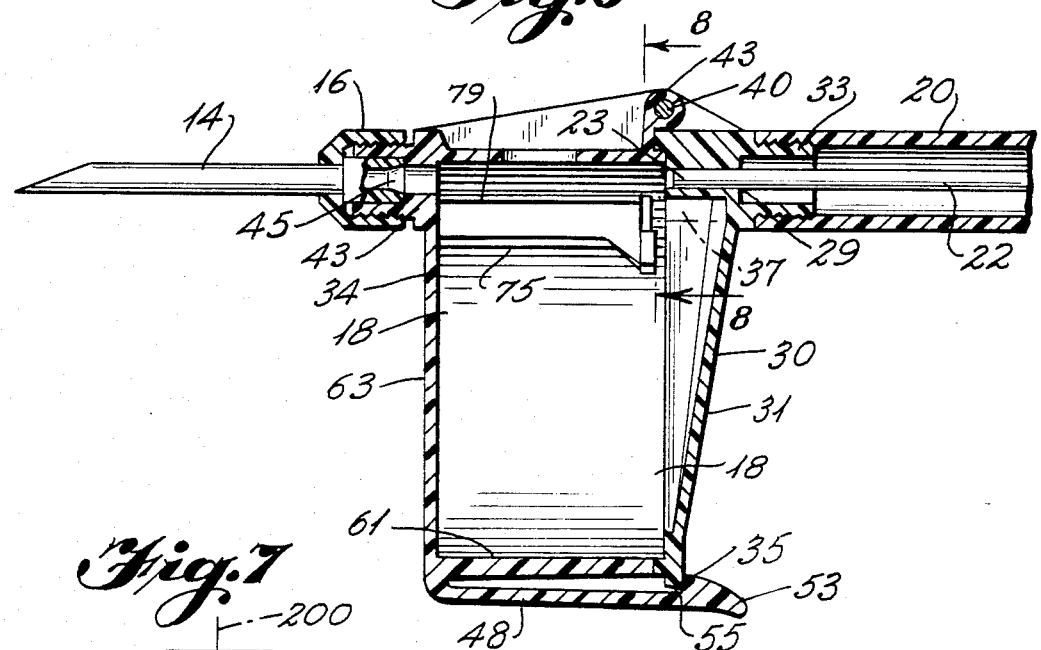
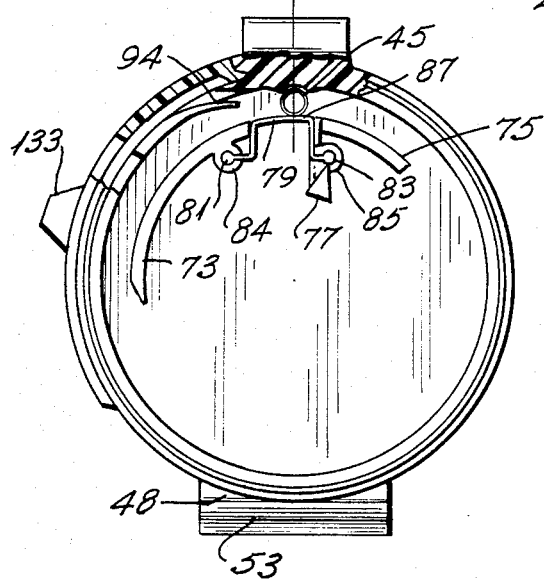
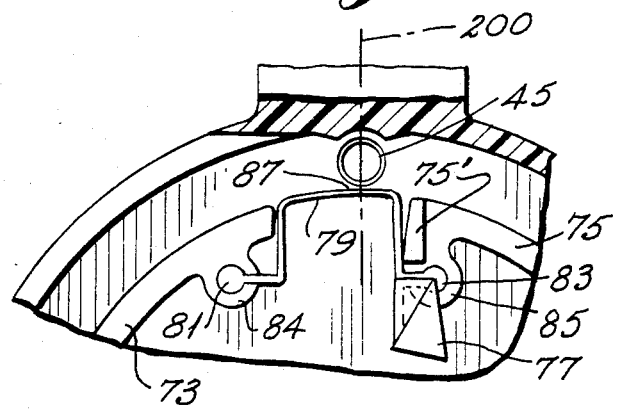
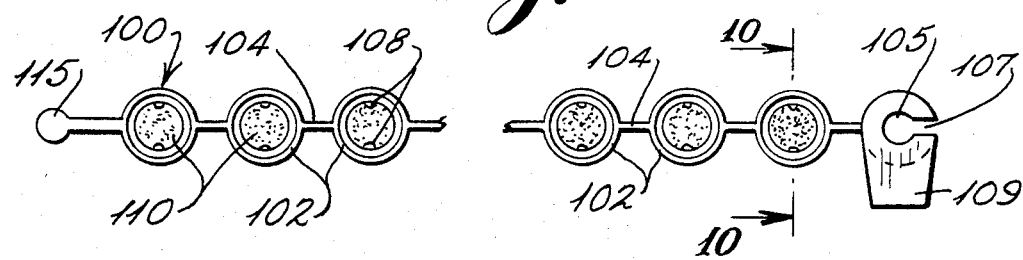

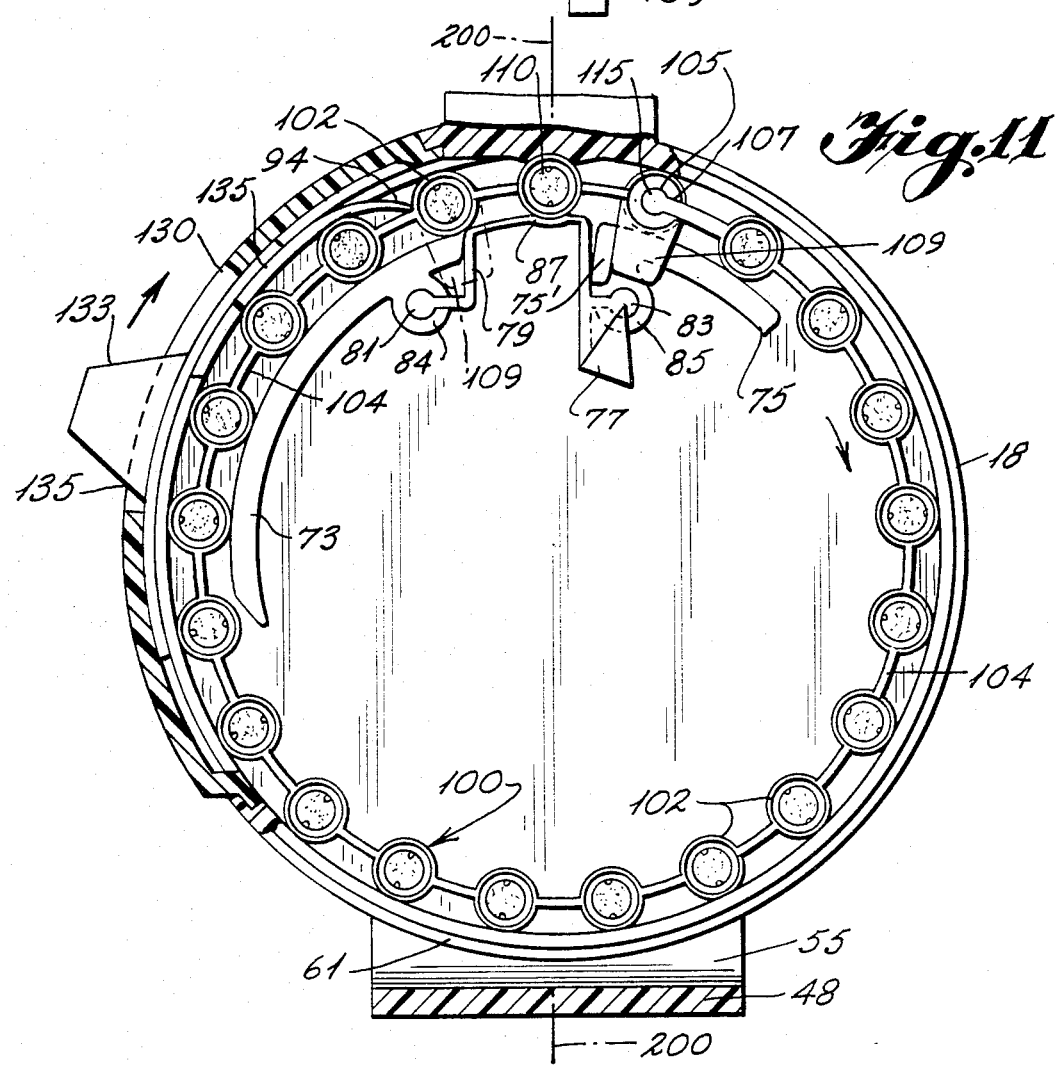

MEDICAMENT IMPLANT APPLICATOR

INTRODUCTION

Good animal husbandry practices sometimes requires insertion into the animal (e.g., intradermally, subcutaneously, intramuscularly, etc.) of a solid or semi-solid medicament. Such practice is common for growth stimulation of cattle, for example. Solid or semi-solid pellets containing the growth stimulating hormones are implanted in the neck or ear of the animal, to remain there for an extended period, even throughout the life span of the animal. The ear is preferred implantation site, since the ear is a throwaway organ. Any implant residue present in the ear when the animal is slaughtered never enters channels of commerce, to become ingested by people or domestic animals.

A typical medicament implanter device comprises a hand-held instrument built of a size consistent with the size of the animal (large for cattle, small for chickens. An apertured needle on the instrument makes a sizable, non-coring puncture opening into the skin e.g., of the ear of the animal and forms a cavity in the skin occupied temporarily by the needle on the instrument. The body of the instrument may be shaped like a hand gun, or alternatively, like a hypodermic syringe with a receiver-dispenser for the medicament implant. The needle of the implanter is inserted into the skin of the animal, then withdrawn. As the needle is being withdrawn from the animal, pellets of medicament are expelled into the cavity formed by the needle.

For cattle, an implant dosage unit form may constitute a multiplicity, e.g., eight relatively small solid or semi-solid pellets. A reciprocal plunger inside the body of the implanter forces the pellet dosage unit out of a cartridge encasement wherein they were prepackaged into the bore of the needle and from there into the animal.

A number of medicament implant devices have been suggested to the art, including devices adapted for use with cartridges or other encasement forms that contain a multiplicity of dosage units of the implants, U.S. Pat. No. 3,774,607, for example. This invention relates to the multi-dose aspect of the medicament implanter art.

The principal object of the present invention is to provide a novel implant applicator for implantation of the pellets.

A further object of the invention is to provide a novel multi-dosage indexable encasement adapted for use in the implant applicator of this invention.

The applicator of this invention incorporates certain features that are desirable in a multidose applicator, namely, orientation elements that force the user to load the applicator properly and which advise the user when reloading is required. Indeed, the structure of the applicator prevents its use after all the pellets have been discharged from the encasement. Features most desirable to the supplier of the medicament pellets are present. The multidose encasement of this invention may be filled somewhat more readily than single dose cartridges and can be packaged into a most compact form for shipment.

BRIEF DESCRIPTION OF THE APPLICATOR AND ENCASEMENT

The novel pellet implant encasement of this invention resembles a cartridge belt in appearance. A multiplicity, e.g., 20, of equally spaced apart chambers, are connected in a flexible web. Each chamber is sized to contain therein a dosage unit of medicament, suitably eight pellets. The encasement fits into the applicator and an animal handler can implant animals in succession, e.g., 20 animals, one after another, from each encasement.

The implant applicator of this invention looks like a hypodermic syringe constructed with a large hub at the forward end of the syringe barrel. The medicament encasement is loaded inside of the hub. Ahead of the hub is the hollow needle; the plunger is, of course, to the rear of the syringe barrel. Forward movement of the plunger expels the implant pellet(s) from one chamber of the encasement into and through the needle at the front end of the applicator. Then the plunger is pressed further forward as the needle is being withdrawn from an animal into which the needle had previously been inserted, thereby expelling the pellet(s) into the needle track. Later, when the plunger has been retracted fully, the operator of the implanter shifts the encasement the distance between chambers so that a next adjacent chamber in the encasement comes into registry with needle and plunger for expulsion of medicament pellets therefrom by the plunger.

THE IMPLANT APPLICATOR

For further understanding of this invention, reference is now made to the attached drawings wherein:

FIG. 1 is a diagrammatic view of the implant applicator.

FIG. 2 is a plan view of the implant applicator.

FIG. 3 is a front end view of the implant applicator.

FIG. 4 is a rear end view of the implant applicator.

FIG. 5 is a side view of the implant applicator, showing the applicator in opened position. The closed position is illustrated in shadow.

FIG. 6 is a partial side section taken along line 6—6 of FIG. 2 for an empty implant applicator.

FIG. 7 is a rear view similar to FIG. 4, with parts in section and the cover removed.

FIG. 8 is an enlarged partial section taken along line 8—8 of FIG. 6.

FIG. 9 is a plan view of an implant encasement.

FIG. 10 is a section taken along line 10—10 on FIG. 13.

FIG. 11 is a section taken along line 11—11 of FIG. 2 for a loaded implant applicator.

FIG. 12 is a partial section taken along line 12—12 of FIG. 2 for a loaded implant applicator.

FIG. 13 is a side view of an encasement loaded with the medicament pellets.

Referring now to the drawing, and in particular to FIGS. 1 and 2, it may be seen that in many respects, the implant applicator resembles a hypodermic syringe and also the many variations of such shape that have been suggested heretofore for implanting solid or semi-solid medicaments into domesticated animals. (See for example, the devices disclosed by U.S. Pat. Nos. 3,016,895 and 2,761,446.) Thus, the applicator comprises front to rear, right to left on FIG. 1, but left to right on FIG. 2, a hollow needle 14 secured by a chuck 16 (or by any equivalent known to the art mounting structure) to the front of drum 18. Drum 18 contains the medicament encasement therein.

A tubular barrel 20 secured to the rear of drum 18 is aligned to needle 14 so that the plunger 22 which is centered in barrel 20 is also centered for movement into needle 14. Typically, plunger 22 can be advanced as far as the front end of needle 14. The barrel 20 serves as a hand grip for holding the implant applicator when plunger 22 is advanced. Plunger 22 terminates in a knob 24, the knob 24 serving as a grip for moving the plunger 22.

The plunger length and travel distance are predetermined so that when plunger 22 is fully extended to the rear, its forward end 23 will clear all moving parts inside of drum 18 (see FIG. 6). Standard known-to-the-art stop elements such as spring 25 inside barrel 20 and a shoulder 27 on plunger 22 prevent unintended forward movement by plunger 22.

In the mode of applicator herein illustrated, barrel 20 terminates in a threaded boss 33 on the hub 30 containing a passageway 29 for plunger 22 (see FIG. 6). The wall of passageway 29 serves to guide and center plunger 22. Conveniently, plunger 22 may be formed from bar stock and knob 24 would then be a separate member threaded onto plunger 22.

Mention has already been made that the circumferential outer surface on barrel 20 may serve as a hand grip member. A knob 32 mounted on the rear terminus of barrel 20 can serve for finger grip purposes, including, if so desired, placement of wings thereon for better gripping. (See, for example, the structure suggested by U.S. Pat. No. 3,016,895). In any event, knob 32 serves as a stop element, halting forward travel of plunger 22 when knobs 23 and 32 come together, which is just when the front end 23 of plunger 22 arrives at the forward edge of needle 14, and halting rearward travel of plunger 22 when shoulder 27 arrives at knob 32, which is just when front end 23 of plunger 22 retracts into hub 30. Conveniently, barrel 20 is a section of tube stock that has been threaded at both ends, internally, for example. The knob 32 threads in at the rear of the tube and the boss 33 of hub 30 threads in at the forward end of the tube (see FIG. 6).

Hub 30, suitably a plastic molding from polyethylene, for example, is an integral multipurpose member. On hub 30 is the externally threaded boss 33 to which the tube stock barrel 20 is attached. As has been pointed out, boss 33 contains the passageway 29 for plunger 22. Hub 30 is also part of drum 18, being principally the cover 31 that constitutes the generally circular rear face of drum 18.

As may be seen in FIG. 5, the implant applicator 10 splits at the rear face of drum 18 with hub member 30 and barrel 20 pivotting on a hinge 40 away from the rest of drum 18 and needle 14. At the top of hub 30 is hinge half 33'. Formed at the bottom of the cover portion 31 of hub member 30 is a detent 35 that serves to latch the cover 31 to the balance of drum 18. Formed on the forward face of hub 30 is an upstanding pin 37 (see FIGS. 5 and 6) which constitutes a stop element, as will be explained hereinafter.

Thus, drum 18 is formed from two cooperating members, the cover portion 31 of hub 30 discussed above and a drum base 34. Like hub 30, the drum base 34 is a multipurpose molded article from polyethylene, for example.

At the top of drum base 34 is a hinge-half 43' which mates with hinge-half 33', both halves being mounted on hinge pin 40. When detent 35 at the bottom of cover 31 is released, the drum base 34 and needle 14 of applicator 10 can be pivoted on hinge pin 40 away from cover portion 31 and barrel 20 about 180°, as is illustrated in FIG. 5 to what can be called an open position. The inside of drum base 34 is then exposed for loading a fresh medicament encasement therein, as will be explained hereinafter.

At the front of the drum base 34 is an externally threaded boss 43. A passageway 45 in boss 43 is in alignment with the barrel 20 and needle 14. Chuck 16, to which needle 14 is secured, threads onto boss 43. The needle mounting structure comprises known to the art features, which per se, form no part of this invention. Any of the many known equivalent needle mounting structures may be substituted for the arrangement herein illustrated.

Mention has already been made that drum base 34 is formed with the hinge-half 43' at the top thereof. At the bottom of drum base 34 is formed the seat for detent 35, including a detent aperture 55 into which detent 35 seats to latch hub 30 and drum base 34 to releasably permit opening and closing of the applicator. A tab 48 joined to the front of drum base 34 extends front to rear of drum base 34 and beneath detent 35 around to the back of cover 31. By virtue of its length, tab 48 exhibits spring capability so that latch detent 35 can be seated in or released from 35 for closing or opening the applicator by pressing down on the thumb grip 53.

On the whole, drum base 34 looks like an open drum for having a squat cylindrical wall portion 61, and a circular (front) face wall portion 63. Cover portion 31 of hub 30 seats on cylindrical wall 61 to close off the inside of the drum base 34.

For better understanding of the structure present inside of hub 18 for mounting and shifting of the medicament encasement, the structure of the encasement of this invention will be described beforehand.

THE MEDICAMENT ENCASEMENT

Referring now to FIGS. 9, 10 and 13, it may be seen that the medicament encasement 100 resembles a cartridge belt for comprising a series of equally spaced apart parallel cylindrical or conical chambers 102, twenty chambers, for example, connected into a flexible web by web sections 104. Desirably, encasement 100 is a unitary molded article, from polyethylene, for example. For ease of molding, the chambers 102 may be made ever so slightly conical as is herein illustrated (so that the molding equipment releases more readily). If chambers 102 are conical, the larger diameter ends should all be at the side of encasement 100 that will be entered by plunger 22. Conical encasement chambers 102 are normally filled from the larger diameter side. The medicament pellets 110 are retained in each chamber 102 by internal tabs 106 molded in the chamber wall adjacent the narrow end of each chamber 102. The tabs 106 reduce chamber clearance to less than diameter of the pellets which causes the pellets 110 to be retained inside chamber 102. Internal tabs 106 may be formed on the inside chamber walls during the molding operation that makes the encasement 100.

Upsets 108 are made in each chamber wall at the wide diameter end of chambers 102 after insertion of the medicament pellets 110 inside chambers 102. Upsets 108 may be formed by the machinery that inserts the medicament pellets inside the chambers. Accordingly, the medicament pellets 110 cannot fall out either end of chamber 102 during later handling of the encasement 100. However, plunger 22 can push the relatively soft medicament pellets 110 past retaining tabs 106 to expel the implant pellet contents from chamber 102.

At one side end of encasement 100 is a dummy chamber 105 that is not intended to be filled with pellets.

Optionally, a slot 107 is provided in the end side wall of dummy chamber 105. At the other side end of encasement 100 is a solid cylindrical plug 115 sized-to-fit inside of dummy chamber 105. Slot 107 is sized so plug 115 can be forced through slot 107 into dummy chamber 105. Presence of cylindrical plug 115 and dummy chamber 105 allows encasement 100 to be curved into the circlet mode that is required for use of encasement 100 in the applicator of this invention.

In the circlet mode of encasement 100, presence of plug 115 inside of the dummy chamber 105 helps to block this chamber off against passage by plunger 22; the plunger cannot expel plug 115 from dummy chamber 105. Thus medicament encasement 100 contains a fail-safe feature that advises when all the medicament from a particular encasement has been utilized, that time has come to reload the implant applicator.

To facilitate proper orientation of encasement 100 for filling and later for a proper insertion into the implant applicator, an upstanding tab 109 is provided at an end corner of encasement 100, suitably at the dummy chamber 105 end on the wider diameter or filling side of the chamber row, as may best be seen on FIGS. 10 and 13.

Standard filling machinery is adapted to fill a multiplicity of cartridges simultaneously, from a twenty slot filling head for example. Typically, however, separate single dose cartridges have been used for implantation purposes, c.f. U.S. Pat. No. 2,761,446 and 3,744,493. This requires that a multiplicity of the separate cartridges must be placed into a filling fixture for the filling machine, which allows them to be filled as a single batch. The same operation can be done on essentially the same machinery with encasement 100 serving as package for the batch. By placing an indent or slot at the top of a filling fixture to match tab 109, the tab 109 may be used to orient encasement 100 in a filling fixture for the machine so that all of the chambers 102 are filled from the filling side simultaneously. Dummy chamber 105 is, of course, not filled. A twenty-unit dosage encasement is somewhat easier to pass into and through conventional filling machinery than twenty separate cartridges.

The multidose package of encasement 100 shown in FIG. 9 is in flat form; a best form for packaging and shipment. Five or ten encasements can stack into a small oblong pack, which may be the package for shipment to an ultimate user. An appropriate number of such oblong packs can be boxed together for shipment to a wholesale distributor.

For use in the implant applicator, a circlet form is desired. The user curves encasement 100 into a circlet with plug 115 inserted into dummy chamber 105, e.g., forced through slot 107. Tab 109 serves an orientation purpose. Encasement 100 should be curved to place tab 109 at the inside of the circlet. If encasement 100 is curved so as to place tab 109 at the outside of the circlet, encasement 100 will not fit inside drum base 34 for reason that the effective diameter of the circlet will be too great.

ENCASEMENT MOUNT AND USE STRUCTURE

The circlet form encasement 100 is sized to fit in drum base 35 adjacent cylindrical wall 61 provided tab 109 is at the open or rear face of drum base 34. If the user attempts to insert encasement 100 so that tab 109 will be adjacent the forward drum wall 63, tab would interfere with structure at the inside of drum base 34 and the encasement will not fit (see FIGS. 11 and 12) into drum base 34.

Inside of drum base 34, near the top thereof (see FIGS. 6, 7, 8, and 11) are formed a pair of arcuate guide portions 73 and 75, one on each side of the center line 200 of drum base 34. Guides 73 and 75 upstand from the inside face of circular wall 63. If such is desired, the accurate guides 73 and 75 may be extended at their bottom ends into nearly a full circle guide portion. As is shown on FIG. 6, the guides 73, 75 do not extend the full length of circular sidewall 61, leaving a gap adjacent cover 31 into which the pin 37 on cover 31 extends. Together with sidewall 61 guides 73 and 75 create an annular channel into which the medicament encasement 100 fits (see FIG. 11) with a small overhang past the ends of guides 73, 75 which allows a gap into which orienting tab 109 becomes located. Thus, tab 109 is positioned in the above mentioned free space adjacent cover 31, as is the stop element pin 37 on the inside of cover 31. Guide 75 has a tab 75' at its end to indicate where to place tab 109. This is the start position for encasement 100. Tab 75' may also serve as a stop element.

Desirably, an indicator arrow 77 or equivalent indicia is formed on tab 75' to advise the user of the implant applicator. FIG. 11 illustrates exactly where to position dummy chamber 105 and tab 109 when encasement 100 is loaded into implant applicator.

A curved detent spring 79 fills the gap between guides 73, 75 (see FIGS. 7, 8, 11). Spring ends 81, 83 are mounted in channels provided for that purpose in posts 84 and 85 which respectively underlie and form part of guides 73, 75. The curved surface 87 on spring 79 contains a recess 87 at the intersection of drum axis line 200 and the central axis for needle 14 and impeller 22 which recess provides a seat for a chamber 102 indexing that chamber with impeller 22, so that impeller 22 can pass through the indexed chamber to expel the chamber contents 110 into, then through needle 14.

Clockwise rotation of medicament encasement 100 on guides 73, 75, the direction indicated on FIG. 11 is facilitated modestly by displacement of spring 79 to the left of center line 200 in the mode herein illustrated.

Once the user has the circled encasement 100 inserted into implanter with dummy chamber 105 lined up to arrow 77, the chamber 102 adjacent to the dummy chamber 105 will seat in recess 87, as may be seen in FIG. 11, locating dummy chamber 105 as the last chamber of encasement 100 to be indexed in recess 87.

Since insertion of encasement 100 into the implant applicator can be done only when members 30 and 34 have been privoted apart on hinge pin 40 as shown in FIG. 5 providing access to the inside of drum base 34, pin 37 on cover 31 has been swung away from drum base 34. Pin 37 can play no role in loading and unloading of the implant applicator. However, when hub 30 and drum base 34 are pivoted back and locked together in the use position of the implant applicator, pin 37 becomes located adjacent tab 109 between dummy chamber 105 and the chamber 102 adjacent thereto indexed on spring recess 87; see FIG. 12. Tab 75' is also in that locale; see FIG. 11, and if desired, together with or instead of pin 37 is employed for the stop function hereinafter described.

Clockwise movement of encasement 100 will shift each chamber 102 in succession onto the recess 87 of spring 79 until dummy chamber 105 approaches the indexed position, at which time tab 109 on medicament 100 is stopped by pin 37 (see FIG. 12). The encasement 100 can no longer be rotated. Preferably, the relative size and positions of tab 109 and pin 37 will allow chamber 102 to move off recess 87, but prevent indexing thereon of dummy chamber 105. That chamber is filled by the non-expellable plug 115 in any event. Thus, the user cannot avoid recognizing when medicament encasement 100 has been emptied. Sheer inability to employ the applicator would advise the user that the applicator requires a fresh encasement.

Movement of encasement 100 chamber by chamber inside of the implant applicator is done after plunger 22 has been retracted fully. At the left side of cylindrical wall 61 in the view of FIG. 11, may be seen the slot 130 wherein actuator 135 is deposed, seated in grooves provided in wall portion 61 for that purpose. Actuator 135 may be a unitary molded object, e.g., from polyethylene. A push-pull nose 133 on the actuator extends through slot 130 to the outside of wall 61. The main body of actuator 135 is an arcuate portion that rides inside the side wall 61 of drum base 34 and follows the general contour of wall 61. That portion of wall 61 adjacent main body 135 is stepped outward to allow the actuator 135 to follow the wall contour as is illustrated in FIGS. 5 and 11. The main actuator 135 terminates in pusher finger 94. Finger 94 curves radially inward from main body 135, to a terminus point near the juncture of a web section 104 with a chamber 102. The curvature of and normal position of finger 94 provides clearance for proper insertion of encasement 100 into drum base 34.

The length of travel allowed for actuator nose 133 in slot 130 corresponds to the spacing between adjacent the chambers 102 of encasement 100. Thus, when nose 133 is resting at the base end of slot 130, as would be the situation when a fresh encasement has been loaded properly with arrow 77 lined up to the dummy chamber 105. The first chamber 102 is indexed in recess 87. Then, after discharge of the implant pellet medicament contents from the first chamber 102 followed by full retraction of plunger 22, which positions plunger end 23 clear of the chamber 102, as shown by FIG. 6, the user advances encasement 100 one chamber by pushing nose 133 from the base of slot 130 to the head thereof. This movement causes finger 94 to push encasement 100 a like distance, shifting the first medicament chamber 102 off spring detent 87, and the next chamber 102 on to recess 87 in its place, thereby indexing the next succeeding chamber 102 to plunger 22 and the bore of needle 14. Nose 133 may be pushed back before or after the contents of the indexed chamber 102 are expelled therefrom.

When nose 133 is retracted to the base of slot 130, as it must be before the encasement 100 can be advanced further, finger 94 deflects radically outward riding up and back over the next in line encasement chamber 102, then snaps back into its normal curvature and terminates adjacent the juncture of web and chamber. The frictional drag during such reverse movement by finger 94 is insufficient to back the indexed encasement chamber 102 off spring recess 87. Accordingly, encasement 100 does not shift during the reverse movement of actuator 135. Desirably, stop 37 contacts tab 109 before full indexing of dummy chamber 105 on spring recess 87, and movement of finger 94 is stopped. The actuator nose 133 is only part way along slot 135. Inability to shift the encasement 100 into an indexed position is what ordinarily advises the user that the implant applicator must be reloaded.

We claim:
1. A medicament implanter comprising:
   (a) a hollow needle; a plunger in axial alignment with and movable into said hollow needle; and means for moving said plunger into and out of said needle;
   (b) a drum interposed between needle and said plunger moving means, said drum being adapted to retain therein adjacent the drum periphery a circlet form encasement containing a multiplicity of medicament implant dosage units, said encasement being a multiplicity of equally spaced apart parallel chambers and web sections connecting adjacent chambers, each chamber being adapted to contain therein one dosage unit of medicament implant;
   (c) an index means inside said drum for indexing one chamber of said circlet form encasement in axial alignment with needle and plunger whereby said plunger may move through the indexed chamber to expel medicament from said chamber; and
   (d) actuator means located on the periphery of said drum for rotatably shifting said circlet form encasement within said drum to shift the indexed chamber thereof from said index means and the next adjacent chamber to said index means.

2. The implanter of claim 1 wherein said actuator means comprises an actuator member extending from a nose portion thereon positioned outside of said drum to a flexible pusher finger portion thereon inside of said drum, a slot being provided in the drum periphery through which said actuator member extends and in which said actuator member can reciprocate a chamber to chamber shifting distance on said circlet form encasement.

3. The implant applicator of claim 1 wherein said indexing means comprises a spring underlying said circlet form encasement in contact therewith and a recess in said spring whereon one chamber of said circlet form encasement may seat and be thereby indexed in alignment with needle and plunger.

4. A medicament implant applicator comprising:
   (a) a hollow needle; a plunger in axial alignment with and movable into said hollow needle; and means for moving said plunger into and out of said needle;
   (b) a drum interposed between needle and said plunger moving means, said drum being adapted to retain therein adjacent the drum periphery a circlet form encasement containing a multiplicity of medicament implant dosage units, said encasement being a multiplicity of equally spaced apart parallel chambers and web sections connecting adjacent chambers, each chamber being adapted to contain therein one dosage unit of medicament implant;
   (c) an index means inside said drum for indexing one chamber of said circlet form encasement in axial alignment with needle and plunger whereby said plunger may move through the indexed chamber to expel medicament from said chamber;
   (d) means for rotationally advancing said circlet form encasement chamber by chamber to and from said index means;
   (e) said drum further comprising: a hinged drum base; a hinged drum cover; and a hinge pin joining drum base to drum cover whereby base and cover may be pivoted apart to provide access to the inside of said drum base; the drum base containing therein arcuate guide means annularly spaced from the drum periphery for retaining said circlet form encasement adjacent the drum periphery; and a stop element inside said drum adapted to stop the rotational chamber by chamber advancement of said circlet form encasement after all implant medicament containing chambers of said encasement have been advanced to said index means.

5. A unitary flexible medicament encasement comprising:
a multiplicity of generally cylindrical chambers open at each end parallel to each other and equally spaced apart, with web sections connecting each chamber, each chamber being adapted to contain therein one dosage unit of implant medicament;
the entrance and exit openings to each chamber having medicament retaining elements formed in the chamber wall, whereby a solid or semi-solid medicament implant is retained inside the chamber until expelled therefrom;
a dummy chamber at one end of said encasement and a plug sized to fit said dummy chamber at the opposing end of said encasement, whereby said encasement may be transformed from a linear chamber array into a circlet by disposing said plug into said dummy chamber, and;
an orienting tab located at one corner of said encasement, said tab being adapted to orient said encasement when the chambers thereof are filled with medicament, and also when an implant applicator is loaded with a fresh encasement, said tab also being adapted to serve as a stop element when the contents of all chambers in a circlet form encasement have been emptied.

6. The encasement of claim 5 further comprising spacing the next adjacent chambers to said plug and said dummy chamber to maintain equal chamber to chamber spacing inclusive of said dummy chamber when said encasement is in a circlet form.

* * * * *